(12) United States Patent
Gallou et al.

(10) Patent No.: US 7,550,622 B2
(45) Date of Patent: Jun. 23, 2009

(54) CYCLOALKYLAMIDOACID COMPOUNDS, PROCESSES FOR MAKING AND USES THEREOF

(75) Inventors: Isabelle Gallou, Danbury, CT (US); Nizar Haddad, Danbury, CT (US); Chris Senanayake, Brookfield, CT (US); Xudong Wei, Ridgefield, CT (US); Jinghua Xu, Ridgefield, CT (US)

(73) Assignee: Boehringer Ingelheim International GmbH (DE)

( * ) Notice: Subject to any disclaimer, the term of this patent is extended or adjusted under 35 U.S.C. 154(b) by 357 days.

(21) Appl. No.: 10/916,928

(22) Filed: Aug. 12, 2004

(65) Prior Publication Data

US 2005/0085544 A1    Apr. 21, 2005

Related U.S. Application Data

(60) Provisional application No. 60/494,363, filed on Aug. 12, 2003.

(51) Int. Cl.
*C07C 69/74* (2006.01)
*C07C 61/04* (2006.01)

(52) U.S. Cl. ........................ 560/123; 562/505
(58) Field of Classification Search ............. 560/123; 562/505
See application file for complete search history.

(56) References Cited

U.S. PATENT DOCUMENTS 3,954,730 A    5/1976   Metzger et al.
6,399,809 B1 *  6/2002   Kleemiss et al. ............. 560/24

FOREIGN PATENT DOCUMENTS

DE           23 53 584 A    5/1975

OTHER PUBLICATIONS

Demyanov et al, S.M. Izv. Akad. Nauk. SSSR, Ser. Khim. pp. 529 (1937) best availible.*
Il'yasov, "synthesis of 1-aminocyclopropane", Khimiia Prirodnykh Soedinenii, vol. 6 pp. 855-857, (1995).*
Zefirov et al, Chem. Abs. 99:38075 (1983).*
Oediger et al, Chem. Abs. 84:150239 (1976).*
Guo et al, Chem. Abs. 110:134732.*
Fedorynski et al, Chem. Abs. 92:41373 (1980).*
Hung-Wen Liu, et al. "Stereochemical Studies on the Reactions Catalyzed by the PLP-Dependent Enzyme 1-Aminocyclopropane-1-carboxylate Deaminase", J. Am. Chem. Soc. 1984, vol. 106, pp. 5335-5348, XP002307171.
H.C.H. Carpenter, et al. "The action of ethylene dibromide and trimethylene dibromide on the sodium compound of ethylic cyanate", J. Chem. Soc. Transations, vol. 75, 1899, pp. 921-934, XP001167017.

H. Oediger, et al. "Dialkylierung in Gegenwart von 1,8-Diazabicyclo[5.4.0]undec-7-en", Justus Liebigs Ann. Chem., 1976, pp. 348-351, XP008039575.
W. Dvonch, et al. "Preparation of New Amino Acids and 2,5-Oxazolidinediones", J. Org. Chem. vol. 29, No. 9, 1964, pp. 2764-2766, XP002307172.
G. W. Kabalka, et al. "An efficient route to 3-substituted cyclobutanone derivatives", Tetrahedron Letters, vol. 44, 2003, pp. 1879-1881.
R.R.Srivastava, et al. "4-Dihydroxyborylphenyl Analogues of 1-Aminocyclobutanecarboxylic Acids: Potential Boron Neutron Capture Therapy Agents", J. Org. Chem. 1999, vol. 64, pp. 8495-8500.
R.R.Srivastava, et al. "Synthesis of 1-Amino-3-[2-(7-(2-hydroxyethyl)-1,7-dicarba-closo-dodecaboran (12)-1-yl)ethyl] cyclobutanecarboxylic acid and its nido-analogue: Potential BNCT Agents" J. Org. Chem. 1997, vol. 62, pp. 8730-8734.
R.R.Srivastava, et al. "Synthesis of 1-Amino-3-[2-(1,7-dicarba-closo-dodecaboran(12)-1-yl)ethyl] cyclobutane-carboxylic Acid: A Potential BNCT Agent", J. Org. Chem., 1997, vol. 62, pp. 4476-4478.
N.J. Demyanov, et al. "Synthesis of Cyclobutanon" Bulletin de L'Academie Des Sciences de L'urss, 1937, pp. 530-538.
W. Dvonch, et al. "Preparation of New Amino Acids and 2,5-Oxazolidinediones" J. Org. Chem. 1964, vol. 29, pp. 2764-2766.
K. Tanaka, et al. "Synthesis of Homochiral 4-Amino-4-Carboxy-2-Phosphonomethylpyrroli-Dines Via a Diastereoselective Bucherer-Bergs Reaction of 4-Oxopyrrolidine Derivative: Novel Conformationally Restricted AP 5 Analogues" Tetrahedron: Asymmetry vol. 6, No. 9, pp. 2271-2279, 1995.
W. Haefliger, et al. "Stereospezifische Synthese Einer Neuen Morphin-Teilstruktur", Helvetica Chimica Acta—vol. 65, Fasc. 6, 1982, No. 181, pp. 1837-1852.
W. Haefliger, et al. "Stereospezifische Synthese Einer Neuen Morphin-Teilstruktur", Helvetica Chimica Acta—vol. 65, Fasc. 6, 1982, No. 181, pp. 1837-1852—Translated Abstract, Interscience.

(Continued)

*Primary Examiner*—Janet L. Andres
*Assistant Examiner*—Raymond Covington
(74) *Attorney, Agent, or Firm*—Michael P. Morris; Mary-Ellen M. Devlin; David A. Dow

(57) ABSTRACT

The invention relates to the field of pharmaceutics and more specifically to cycloalkylamidoacid compositions useful in the preparation of cycloalkyaminoacids and oxazolidinediones, and processes for making cycloamidoacids

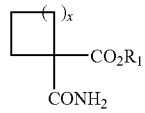

Formula I X and R are defined herein.

11 Claims, No Drawings

OTHER PUBLICATIONS

X. Huang, et al. "A Mild and Efficient Modified Hofmann Rearrangement", J. Org. Chem. 1997, vol. 62, pp. 7495-7496.

M. L. Izquierdo, et al. "Synthesis of E and Z 1-Amino-2-Aryl(Alkyl)-Cyclopropanecarboxylic Acids via Meldrum Derivatives", Tetrahedron vol. 41, No. 1, pp. 215-220, 1985.

Y.T. Huang, et al. "Chemical Studies on Amino Acids and their Derivatives X. Synthesis of •-Amino-•-methyl-caproic Acid and •-Amino-Capric Acid" Dept. Biochem. Nat. Med. College of Shanghai and Institute of Chemistry, Academia Sinca, Shanghai, 1947, vol. 15, pp. 46-54.

Y.T. Huang, et al. "Chemical Studies on Amino Acids and their Derivatives. IX. Synthesis of Valine, Leucine and Norleucine", Chemical Studies on Amino Acids, 1947, vol. 15, pp. 38-45.

Y.T. Huang, et al. "Chemical Studies on Amino Acids and their Derivatives VIII. Synthesis of •-Amino-•-isoproyl-n-valeric acid and •-Amino-•- isopropyl—n-Caproic Acid" Annual Meeting of the Chinese Chemical Society in Shanghai, 1946, vol. 15, pp. 31-37.

D.R.Zitsane, et al. "Exotic Amino Acids: I. Synthesis of •-Amino Acids with a Cyclohexene Substituent", Zhurnal Organicheskoi Khimii, vol. 35, No. 10, 1999, pp. 1489-1492.

D.R.Zitsane, et al. "Exotic Amino Acids: I. Synthesis of •-Amino Acids with a Cyclohexene Substituent", Russion Journal of Organic Chemistry, vol. 35, No. 10, 1999, pp. 1457-1460, English translation of Zhurnal Organicheskoi Khimii, vol. 35, No. 10, 1999, pp. 1489-1492.

I.D. Sadekov, et al. "Synthesis and Structure of Aromatic and Heterocyclic Compounds of Tellurium. XXII. A New Method for the Synthesis of Diaryltellurium Dichlorides", J. Org. Chem. of USSR, vol. 19, No. 3, Part 1, 1983, pp. 541-546.

L. Li, et al. "Chemical Studies on Amino Acids and Their Derivatives" J. Chinese Chem. Soc., vol. 9, No. 1, pp. 14-30, 1942.

K.H. Lin, et al. "A New General Method for the Synthesis of •-Amino Acids based on Hofmann's Degradation Reaction", Science and Tech. in China, vol. 1, No. 1, pp. 5-10, 1948.

N.S. Zefirov, et al. "Cycloalkylation by the •,•-Dibromides of compounds containing an activated methylene group as a method for the synthesis of 1,1-disubstituted cycloalkenes", Translated from Zhurnal Organicheskoi Khimii, vol. 19, No. 3, pp. 541-548, 1983.

* cited by examiner

CYCLOALKYLAMIDOACID COMPOUNDS, PROCESSES FOR MAKING AND USES THEREOF

APPLICATION DATA

This application claims benefit to U.S. provisional application Ser. No. 60/494,363 filed Aug. 12, 2003.

FIELD OF THE INVENTION

The invention relates to the field of pharmaceutics and more specifically to novel cycloalkylamidoacid compositions useful in the preparation of cycloalkyaminoacids and oxazolidinediones, and processes for making cycloamidoacids and cycloaminoacids.

BACKGROUND OF THE INVENTION

Cycloalkylaminoacids and oxazolidinediones are useful compounds in the preparation of pharmaceutical agents. For instance, Cyclobutaneaminoacids are useful in peptide synthesis and for use in Boron neutron capture therapy (BNCT) for cancer treatment (Refs. Kabalka, G. W.; Yao, M. -L., *Tetrahedron Lett.*, 2003, 1879-1881. Srivastava, R. R.; Singhaus, R. R. and Kabalka, G. W. *J. Org. Chem.* 1999, 64, 8495-8500. Srivastava, R. R.; Kabalka, G. W. *J. Org. Chem.* 1997, 62, 8730-8734. Srivastava, R. R.; Singhaus, R. R. and Kabalka, G. W. *J. Org. Chem.* 1997, 62, 4476-4478.) Oxazolidinediones are useful in the synthesis of various amino acid derivatives. There is a need in the art for a scalable synthetic route for making these products using materials that are inexpensive and easy to work with.

There are few reported routes for the synthesis of cycloalkylaminoacids in the art. In 1937 Demanyanov reported a preparation of the compound shown in Scheme I from cyclobutanediamide by rearrangement to the hydantoin followed by basic hydrolysis.

Scheme I

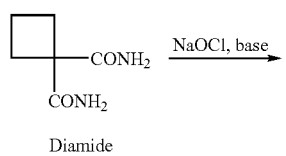

Diamide

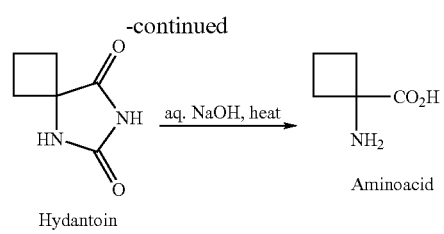

Hydantoin (Demyanov, N. A.; Tel'nov, S. M. *Izv. Akad. Nauk. SSSR, Ser. Khim.* 1937, 529), and described again in 1964 (Dvonch, W.; Fletcher, H.; Alburn, H. E. *J. Org. Chem.* 1964, 29, 2764). Modern variations of this scheme for different targets can be found in: Tanaka, K. -I.; Iwabuchi, H.; Sawanishi, H. *Tetrahedron: Asymmetry* 1995, 6(9), 2271.

Another route for making cyclobutaneaminoacids is through a Curtis rearrangement as shown in Scheme II below. Haefliger, W.; Kloppner, E. *Helv. Chim. Acta* 1982, 65, 1837).

Scheme II

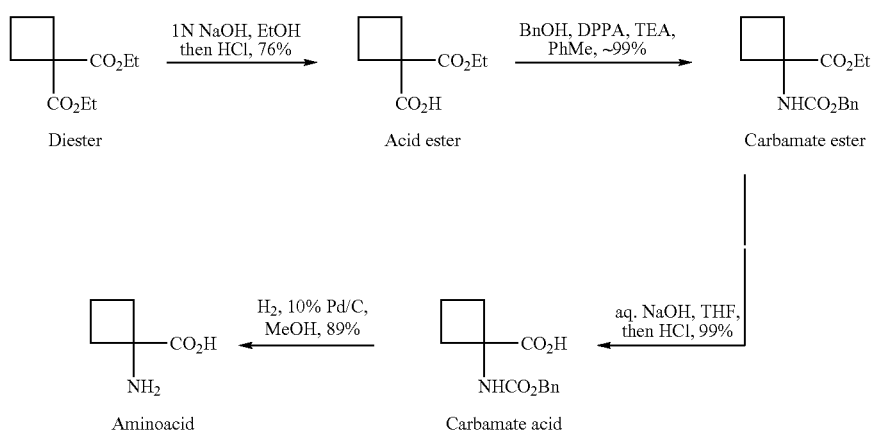

Ethylcyanoacetates have been used in cyclization reactions including the reaction of ethyl 2-cyanoacetate to make 1-cyano-cyclobutanecarboxylic acid ethyl ester: DE2353584. N. S. Zefirov, T. S. Kuznetsova, S. I. Kozhushkov, L. S. Surmina and Z. A. Rashchupkina, J. Org. Chem. USSR (Engl. Transl.), 1983, 19, 541-548. This is considered a very hazardous route, and practical only for making research quantities since azides such as diphenylphosphorylazide (DPPA) are well known as explosives, and would generally be unsuitable for pilot plant use or production.

Hofmann rearrangements of acid amides have also been reported. Huang, Lin and Li, J. Chin. Chem. Soc., 1947, 15, 33-50; Lin, Li and Huang, Sci. Technol. China, 1948, 1, 9; Huang, J. Chin. Chem. Soc., 1948, 15, 227: M. L., Izquierdo, I. Arenal, M. Bernabe, E. Alvearez, E. F., Tetrahedron, 1985, 41, 215-220: Zitsane, D. R.; Ravinya, I. T.; Riikure, I. A.; Tetere, Z. F.; Gudrinietse, E. Yu.; Kalei, U. O.; Russ, J. Org.Chem.; E N; 35; 10; 1999; 1457-1460; ZORKAE; Zh.Org.Khim.; R U; 35; 10; 1999; 1489-1492. For Hofmann reaction using NBS/DBU have also been described: X. Huang, M. Seid, J. W, Keillor, J. Org. Chem. 1997, 62, 7495-7496.

DESCRIPTION OF THE INVENTION

The broadest aspect of the invention provides for cycloalkylamidoacid compounds of Formula I Formula I wherein
$R_1$ is $C_{1-4}$ alkyl, H;

X is $C_{1-2}$ optionally partially or fully halogenated and optionally substituted with one or more OH, $NH_2$, $C_{1-6}$, $SO_2$, phenyl, $CF_3$; and pharmaceutically acceptable salts, salts, solvates, hydrates, stereoisomers, optical isomers; enatiomers, diastereoisomes and racemeic mixtures, esters, tautamers, individual isomers, and mixtures of isomers thereof, The invention also relates to processes for preparing cycloalkylamidoacids of Formula I Formula I

X = 0, 1, 2 and is comprised of:

Step a) alkylating a cyanoester of Formula (Ia)

Formula (Ia)

NC—CO$_2$R$_1$ wherein $R_1$ is $C_1$-$C_4$ alkyl, H;

with bases such as $Na_2CO_3$, DBU, NaOH, KOH, EtONa, EtOK, $K_2CO_3$ and organic acids such as dibromopropane dichloropropane, chlorobromopropane, 1,3-ditosylpropane, 1,3-dimesylpropane, making a cycloalkylcyanoester of Formula (Ib).

Formula (Ib)

cycloalkyl cyanoester
X = 0, 1, 2 and X is optionally partially or fully halogenated and optionally substituted with one or more OH, $NH_2$, $C_{1-6}$, $SO_2$, phenyl, $CF_3$;

Step b) performing base hydrolysis on the product of step a) with a suitable base to make a cycloalkylamidoacid compound of Formula (Ic)

cycloalkylcyanoester → (Base Hydrolysis) → cycloalkamidoacid Formula (1c)

Another embodiment of the invention relates to the process for preparing cycloalkylamidoacids immediately above wherein X is 0 or 1.

In a further embodiment of the invention the cyclalkyloamidoacid product of step b) can optionally be treated with a base and an oxidizing agent to make cycloalkylaminoacid compounds of Formula (Id).

cycloalkylamidoacid → (base, oxidizing agent 70%) → cycloalkyl aminoacid zwitterion Formula (1d)

In a further embodiment of the invention the product of step b) can be further treated with N-bromonating agents, organic base and make amino esters via oxazolidinediones;

cycloalkylamidoacid → (NBS, DBU) → [cycloalkyl oxazolidinedione] → (ROH) → cycloalkyl aminoester wherein R=an allyl, $C_{1-10}$ optionally partially or fully halogenated and optionally substituted with one or more OH, $NH_2$, $C_{1-6}$, $SO_2$, phenyl, $CF_3$.

In other embodiments of the invention other alkyl cyanoesters of Formula (Ia) could be used as starting materials. Suitable alkyl cyanoesters include isopropylcyanoacetate, methylcyanoacetate, ethylcyanoacetate, butylcyanoacetate. The preferred cyanoester is ethylcyanoacetate.

In another embodiment of the invention nucleophilic additives other than $H_2O_2$ can be used for amidoacid production. Suitable nucleophilic additives include sodium percarbonate. The preferred nucleophilic additive is $H_2O_2$.

In another embodiment of the invention the oxidizing agent NaOCl is used for the rearrangement. Other suitable oxidizing agents include CaOCl, NaOBr, KOCl. Preferred oxidizing agents are CaOCl and NaOCl.

Terms and Definitions

Chemical Nomenclature and Conventions Used

Terms not specifically defined herein should be given the meanings that would be given to them by one of skill in the art in light of the disclosure and the context. As used in the specification and appended claims, however, unless specified to the contrary, the following terms have the meaning indicated and the following conventions are adhered to.

The term "compounds of the invention" and equivalent expressions are meant to embrace the general formulas as herein described, including the tautomers, the prodrugs, the salts, particularly the pharmaceutically acceptable salts, and the solvates and hydrates thereof, where the context so permits. In general and preferably, the compounds of the invention and the formulas designating the compounds of the invention are understood to only include the stable compounds thereof and exclude unstable compounds, even if an unstable compound might be considered to be literally embraced by the compound formula. Similarly, reference to intermediates, whether or not they themselves are claimed, is meant to embrace their salts and solvates, where the context so permits. For the sake of clarity, particular instances when the context so permits are sometimes indicated in the text, but these instances are purely illustrative and it is not intended to exclude other instances when the context so permits.

The terms "optional" or "optionally" mean that the subsequently described event or circumstances may or may not occur, and that the description includes instances where the event or circumstance occurs and instances in which it does not. For example, "optionally substituted cycloalkyl" means that the cycloalkyl radical may or may not be substituted and that the description includes both substituted cycloalkyl radicals and cyckloalkyl radicals having no substitution.

The term "substituted" means that any one or more hydrogens on an atom of a group or moiety, whether specifically designated or not, is replaced with a selection from the indicated group of substituents, provided that the atom's normal valency is not exceeded and that the substitution results in a stable compound. If a bond to a substituent is shown to cross the bond connecting two atoms in a ring, then such substituent may be bonded to any atom on the ring. When a substituent is listed without indicating the atom via which such substituent is bonded to the rest of the compound, then such substituent may be bonded via any atom in such substituent. Generally, when any substituent or group occurs more than one time in any constituent or compound, its definition on each occurrence is independent of its definition at every other occurrence. Such combinations of substituents and/or variables, however, are permissible only if such combinations result in stable compounds.

The yield of each of the reactions described herein is expressed as a percentage of the theoretical yield.

The term "pharmaceutically acceptable salt" means a salt of a compound of the invention which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. As the compounds of the present invention are useful in both free base and salt form, in practice, the use of the salt form amounts to use of the base form. Lists of suitable salts are found in, e.g., S. M. Birge et al., J. Pharm. Sci., 1977, 66, pp. 1-19, which is hereby incorporated by reference in its entirety.

The term "solvate" means a physical association of a compound with one or more solvent molecules or a complex of variable stoichiometry formed by a solute (for example, a compound of Formula (I)) and a solvent, for example, water, ethanol, or acetic acid. This physical association may involve varying degrees of ionic and covalent bonding, including hydrogen bonding. In certain instances, the solvate will be capable of isolation, for example, when one or more solvent molecules are incorporated in the crystal lattice of the crystalline solid. In general, the solvents selected do not interfere with the biological activity of the solute. Solvates encompasses both solution-phase and isolatable solvates. Representative solvates include hydrates, ethanolates, methanolates, and the like.

The term "hydrate" means a solvate wherein the solvent molecule(s) is/are $H_2O$.

The compounds of the present invention as discussed below include the free base or acid thereof, their salts, solvates, and prodrugs and may include oxidized sulfur atoms or quaternized nitrogen atoms in their structure, although not explicitly stated or shown, particularly the pharmaceutically acceptable forms thereof. Such forms, particularly the pharmaceutically acceptable forms, are intended to be embraced by the appended claims.

The term "isomers" means compounds having the same number and kind of atoms, and hence the same molecular weight, but differing with respect to the arrangement or configuration of the atoms in space. The term includes stereoisomers and geometric isomers.

The terms "stereoisomer" or "optical isomer" mean a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure exist in the compounds of the invention which may give rise to stereoisomerism, the invention contemplates stereoisomers and mixtures thereof. The compounds of the invention and their salts include asymmetric carbon atoms and may therefore exist as single stereoisomers, racemates, and as mixtures of enantiomers and diastereomers. Typically, such compounds will be prepared as a racemic mixture. If desired, however, such compounds can be prepared or isolated as pure stereoisomers, i.e., as individual enantiomers or diastereomers, or as stereoisomer-enriched mixtures. As discussed in more detail below, individual stereoisomers of compounds are prepared by synthesis from optically active starting materials containing the desired chiral centers or by preparation of mixtures of enantiomeric products followed by separation or resolution, such as conversion to a mixture of diastereomers followed by separation or recrystallization, chromatographic techniques, use of chiral resolving agents, or direct separation of the enantiomers on chiral chromatographic columns. Starting compounds of particular stereochemistry are either commercially available or are made by the methods described below and resolved by techniques well-known in the art.

The term "enantiomers" means a pair of stereoisomers that are non-superimposable mirror images of each other.

The terms "diastereoisomers" or "diastereomers" mean optical isomers which are not mirror images of each other.

The terms "racemic mixture" or "racemate" mean a mixture containing equal parts of individual enantiomers.

The term "non-racemic mixture" means a mixture containing unequal parts of individual enantiomers.

Some of the compounds of the invention can exist in more than one tautomeric form. As mentioned above, the compounds of the invention include all such tautomers.

It is well-known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of the invention from this disclosure and the knowledge of the prior art.

Thus, although the racemic form of drug may be used, it is often less effective than administering an equal amount of enantiomerically pure drug; indeed, in some cases, one enantiomer may be pharmacologically inactive and would merely serve as a simple diluent. For example, although ibuprofen had been previously administered as a racemate, it has been shown that only the S-isomer of ibuprofen is effective as an anti-inflammatory agent (in the case of ibuprofen, however, although the R-isomer is inactive, it is converted in vivo to the S-isomer, thus, the rapidity of action of the racemic form of the drug is less than that of the pure S-isomer). Furthermore, the pharmacological activities of enantiomers may have distinct biological activity. For example, S-penicillamine is a therapeutic agent for chronic arthritis, while R-penicillamine is toxic. Indeed, some purified enantiomers have advantages over the racemates, as it has been reported that purified individual isomers have faster transdermal penetration rates compared to the racemic mixture. See U.S. Pat. Nos. 5,114,946 and 4,818,541.

Thus, if one enantiomer is pharmacologically more active, less toxic, or has a preferred disposition in the body than the other enantiomer, it would be therapeutically more beneficial to administer that enantiomer preferentially. In this way, the patient undergoing treatment would be exposed to a lower total dose of the drug and to a lower dose of an enantiomer that is possibly toxic or an inhibitor of the other enantiomer.

Preparation of pure enantiomers or mixtures of desired enantiomeric excess (ee) or enantiomeric purity are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, for example, GC, HPLC, CE, or NMR, and assignment of absolute configuration and conformation, for example, CD ORD, X-ray crystallography, or NMR.

In general, all tautomeric forms and isomeric forms and mixtures, whether individual geometric isomers or stereoisomers or racemic or non-racemic mixtures, of a chemical structure or compound is intended, unless the specific stereochemistry or isomeric form is specifically indicated in the compound name or structure.

General Synthetic Methods

The present invention provides for compositions of cycloalkylamidoacids of general Formula I and to processes for preparing the same.

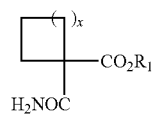

Formula I wherein X, and $R_1$ are as defined herein.

The invention also provides processes for making compounds of Formula (I). Intermediates used in the preparation of compounds of the invention are either commercially available or readily prepared by methods known to those skilled in the art.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Experimental Examples section. Typically, reaction progress may be monitored by thin layer chromatography (TLC), if desired, and intermediates and products may be purified by chromatography on silica gel and/or by recrystallization.

Step a) Alkylation of a Cyanoester

Step a) of the inventive process comprises reacting a compound of the Formula (Ia)

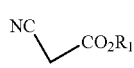

Formula (Ia)

wherein $R_1$ is $C_1$-$C_4$ alkyl, H;

with bases such as $Na_2CO_3$, DBU, NaOH, KOH, EtONa, EtOK, $K_2CO_3$ and cycloalkylating agents such as 1,3-dibromopropane, 1,3-dichloropropane, 1-chloro-3-bromopropane, 1-bromo-3-chloropropane, 1,3-ditosylpropane, 1,3-dimesylpropane, making a cycloalkylcyanoester of formula (Ib).

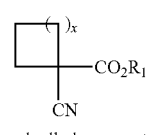

Formula (Ib)

cycloalkyl cyanoester

The alkylcyanoesters for Formula (Ia) can be prepared as described in DE2353584, N. S.

Zefirov, T. S. Kuznetsova, S. I. Kozhushkov, L. S. Surmina and Z. A. Rashchupkina, J. Org. Chem. USSR (Engl. Transl.), 1983, 19, 541-548 which is incorporated herein by reference in its entirety. Alkylcyanoesters can also be obtained commercially from Aldrich and Degussa.

A number of alkylcyanoesters of Formula I can be used in the method of the invention including methyl cyanoester, propyl cyanoester, isopropyl cyanoester, n-butyl cyanoester and t-butyl cyanoester. The preferred compound of alkylcyanoesters of Formula (Ia) is ethycyanoester.

The alkylation reaction can be run at a temperature of between 0° C. and 100° C. degrees and for between 0.5 and 36 hours.

The preferred reaction conditions for Step a) are as follows 60° C. for 5 hours.

Step b) Base Hydrolysis of Cyanoester

Step b) of the inventive process comprises the step of performing base hydrolysis on the product of step a) with a suitable base to make a cycloalkylamidoacid compound of Formula (Ic):

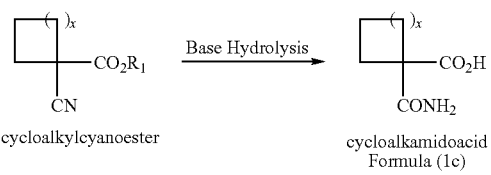

cycloalkylcyanoester
cycloalkamidoacid
Formula (1c)

wherein $R_1$ is $C_1$-$C_4$ alkyl, H in an organic solvent and a base to form a compound of Formula (Ib).

Step b) of the inventive process comprises performing base hydrolysis on the product of step a) with a suitable base to make a cycloalkylamidoacid compound of Formula (Ib). Suitable bases include NaOH, KOH, $Ca(OH)_2$. The preferred base is NaOH.

The reaction of step b) can be run at between −10° C. and 50° C. degrees for between 10 and 600 minutes.

The preferred reaction conditions for step b) are as follows: stirring at 45° C. for 30 minutes followed by the addition of $H_2O_2$ at 0-25° C. and stirring for 2 hours.

In a further embodiment of the invention the product of step b) can be treated with NBS, diazabicycloundecene (DBU) and benzyl alcohol in a tandem Modified Hoffmann rearrangement—intramolecular cyclization and ring opening reaction to aminoesters. Alternatively, the following brominating reagents can be used. 1,3-dibromo-5,5-dimethylhydantoin, n-bromoacetamide, 1-bromo-3-chloro-5,5-dimethylhydantoin, 3-bromo-4,4-dimethyl-2-oxazolidinone, 1-bromo-5,5-dimethylhydantoin, 3-bromo-5,5-dimethylhydantoin, dibromo isocyanuric acid, n-bromoacetamide monohydrate, n-bromocaprolactam, n-bromophthalimide, 3-bromo-1-chloro-5,5-dimethylhydantoin, dibromoisocyanuric acid, potassium salt, n-bromoglutarimide, 1,3-dibromo-5-ethyl-5-methylhydantoin, 1-bromo-3,5-dimethyl-5-ethylhydantoin, 1,3-dibromohydantoin, 1,3-dibromo-5-isopropyl-5-methylhydantoin, dibromocyanoacetamide, 3-bromo-5-methyl-5-phenyl-imidazolidine-2,4-dione.

Alternatively, the following reagents can be used to make aminoesters MeOH, EtOH, PrOH, i-PrOH, BuOH, i-BuOH and $PhCH_2OH$.

The preferred reaction conditions for making an aminoester are addition of DBU at below 30° C.; followed by addition of NBS at 45° C. and stirring for 20 min at 45° C.

SYNTHETIC EXAMPLES

In order that this invention be more fully understood, the following examples are set forth. These examples are for the purpose of illustrating embodiments of this invention, and are not to be construed as limiting the scope of the invention in any way since, as recognized by one skilled in the art, particular reagents or conditions could be modified as needed for individual compounds. Starting materials used are either commercially available or easily prepared from commercially available materials by those skilled in the art.

Example 1

Synthesis of Cyclobutaneamidoacid from Ethylcyanoacetate

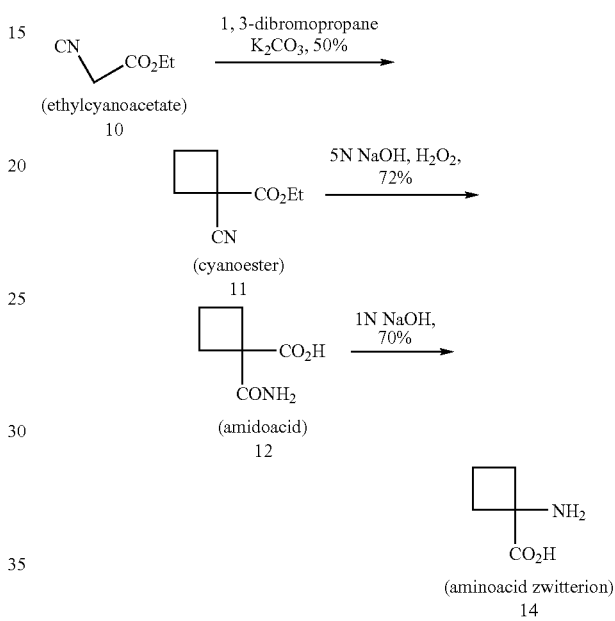

Cyanoester 11. Under nitrogen atmosphere 1,3-dibromopropane(20.2 g, 0.10 mol, 0.2 eq.) was added to a suspension of $K_2CO_3$ (165.9 g, 1.2 mol, 2.4 eq.) in THF (540 ml) and DMSO (60 ml) at ambient temperature. The stirring mixture was heated to 60° C., and a 1:1 mixture of ethylcyanoacetate (56.5 g, 0.50 mol, 1 eq.) and 1,3-dibromopropane (100.8 g, 0.50 mol, 1 eq.) was added slowly via an addition funnel over a period of 8 hours. The reaction mixture was stirred for 5 hours at 60° C., cooled to ambient temperature, and then quenched with 5L $H_2O$. Organic layer was separated, concentrated in vacuum and distilled to give a fraction of 78-85° C./11 mm which was cyanoester 11 (38 g, 50% yield). $^1$H NMR ($CDCl_3$, 400 MHz) δ: 4.27 (q, J=7.2 Hz, 2H), 2.78-2.68 (m, 2H), 2.68-2.57 (m, 2H), 2.31-2.21 (m, 1H), 2.21-2.10 (m, 1H), 1.30 (t, J=7.2 Hz, 3H). $^{13}$C NMR ($CDCl_3$, 100 MHz) δ: 168.7, 120.3, 62.8, 39.6, 31.2, 17.2, 14.0. MS(EI): 154($M^+$+ 1).

Amidoacid 12. Cyanoester 11 (4.60 g, 30 mmol, 1 eq.) and 5N NaOH (12 ml, 60 mmol, 2 eq.) were added into a 100 ml round bottom flask. The stirring mixture was heated at 45° C. for 30 minutes, and the resulting homogeneous solution was cooled to ambient temperature. 30% $H_2O_2$ (6 ml, ca. 60 mmol, 2 eq.) was added slowly over a period of one hour while temperature was maintained at about 25° C. with a water bath. The mixture was stirred for 30 minutes and acidified with concentrated HCl to pH=3.0. The slurry was filtered to furnish 3.09 g of amidoacid 12 (72% yield) as a colorless solid. $^1$H NMR (DMSO, 400 MHz) δ : 7.25 (s, 1H), 6.95 (s, 1H), 2.40-2.25 (m, 4H), 1.81-1.65 (m, 2H). $^{13}$C NMR (DMSO, 100 MHz) δ: 175.6, 174.5, 54.4, 29.9, 16.4. MS(EI): 142 (M−1).

Example 2

Synthesis of Cyclobutaneaminoacid from Cyclobutaneamidoacid

Aminoacid Zwitterion 14. Amidoacid 12 (1.43 g, 10.0 mmol, 1 eq.) was slowly added to a solution of 1N aqueous NaOH (10 ml, 10.0 mmol, 1 eq.) under $N_2$ at 0° C. with a water-ice bath. NaOCl solution (10-13% solution from Aldrich Chem. Co., 9.0 ml, ca. 15.0 mmol, 1.5 eq.) was added slowly, and the resulting mixture was stirred at 5° C. for one hour. 10 N NaOH solution (2.0 ml, 20 mmol, 2 eq.) was added slowly in order to keep the temperature at below 20° C., and the mixture was stirred at 15-25° C. for three hours. LC-MS indicated that the reaction was completed. After quenching with a solution of $Na_2S_2O_3$-5 $H_2O$ (2.48 g, 10 mmol, 1 eq.) in $H_2O$ (3 ml) at 15° C., the reaction mixture was stirred for 1 h and neutralized to pH=7.0 with 12N aq. HCl. The volatiles were removed under vacuum by azeotroping with toluene to give ca. 9 g of white solid. The solid was extracted with methanol (3×30 mL), and 2.0 g crude product was obtained after evaporation of methanol. $^1$H NMR assay showed this solid contained 0.81 g amino acid 10 (70% yield) with the remainder being inorganic salts. Both $^1$H and $^{13}$C NMR data were compared and found to be identical with an authentic sample from Sumitomo Chemical, Inc.

Example 3

Generation and Reaction of Oxazolidinediones From Amidoacid

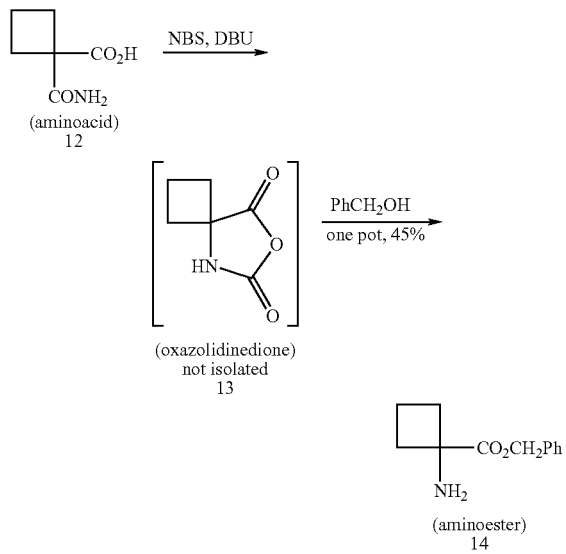

Aminoester 14. Amidoacid 12 (143 mg, 1.00 mmol, 1 eq.), benzylalcohol (324 mg, 3.00 mmol, 3 eq.) and 1,4-dioxane (5 ml) were added into a 50 ml round bottom flask under $N_2$. To the stirred solution was added DBU (304 mg, 2.00 mmol, 2 eq.) while the temperature was kept below 30° C. with a water bath. Water bath was removed, and NBS (178 mg, 1.00 mmol, 1 eq.) was added in one portion. The internal temperature rose to ca. 45° C. After 5 minutes additional NBS (178 mg, 1.00 mmol, 1 eq.) was added, and the reaction mixture was stirred at 45° C. for an additional 20 minutes with the help of a heating mantle. Solvent 1,4-dioxane was removed under vacuum. The residue was dissolved in ethyl acetate (30 ml) followed by washing with $H_2O$ (2×10 mL) and extraction with 1N HCl (2×10 mL). The combined aqueous HCl layer was neutralized with solid $Na_2CO_3$ to pH=10, and the resulting mixture was extracted with ethyl acetate (2×15 mL). After drying with anhydrous $Na_2SO_4$ and the removal of solvent under vacuum an oil (280 mg) was obtained. $^1$H NMR assay showed it contained 92 mg aminoester 14 (45% yield) with the remainder being benzyl alcohol. $^1$H NMR (CD$_3$OD, 400 MHz): 1.90-2.00 (m, 2H), 2.01-2.11 (m, 2H), 2.46-2.56 (m, 2H), 5.20 (s, 2H), 7.20-7.40 (m, 5H) ppm. MS (EI): 206 (M$^+$+1).

What is claimed is:

1. A process

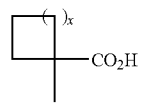

comprising:
 a) alkylating a cyanoester of Formula (Ia)

Formula (Ia)

with a base and an organic acid to make a cycloalkylcyanoester of Formula (Ib)

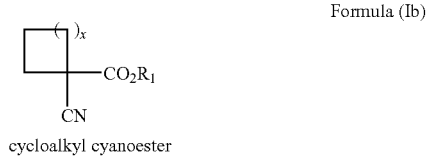

Formula (Ib)

cycloalkyl cyanoester b) performing base hydrolysis on the cycloalkyl cyanoester with a suitable base to make a cycloalkylamidoacid compound of Formula (1c);

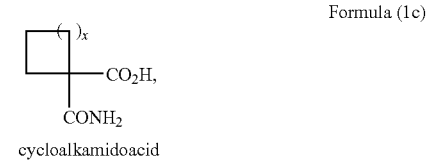

Formula (1c)

cycloalkamidoacid wherein $R_1$ is $_1$-$C_4$ alkyl, or H; and
X=$C_{1-2}$ alkylene, optionally partially or fully halogenated; and c) treating the cycloalkylamidoacid compound of Formula (1c) with an N-brominating agent, an organic base and ROH, to make a cycloalkyl aminoester via an oxazolidinedione, as follows:

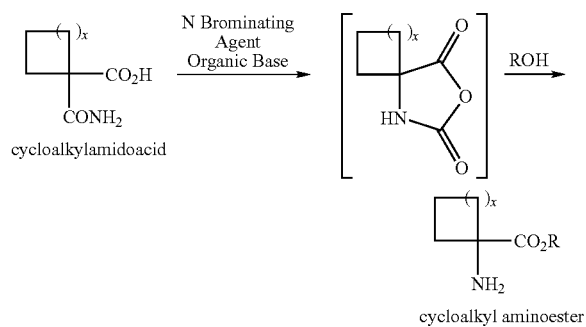

wherein R=$C_{1-10}$alkyl, optionally partially or fully halogenated and optionally substituted with one or more of OH, $NH_2$, $C_{1-6}$, $SO_2$; phenyl, or $CF_3$.

2. The process of claim 1 wherein the base used in alkylating the cyanoester is selected from $Na_2CO_3$, DBU, NaOH, KOH, EtONa, EtOK, or $K_2CO_3$.

3. The process of claim 1 wherein the organic acid used in alkylating the cyanoester is selected from dibromopropane dichloropropane, chlorobromopropane, 1,3-ditosylpropane, or 1,3-dimesylpropane.

4. The process of claim 1 wherein X is $C_1$ alkylene.

5. The process of claim 1, wherein the alkyl cyanoester of Formula (Ia) used as starting material is: isopropylcyanoacetate, methylcyanoacetate, ethylcyanoacetate, or butylcyanoester.

6. The process of claim 1, wherein the N-brominating agent in step c) is N-bromosuccinimide (NBS).

7. The process of claim 1, wherein the organic base in step c) is diazabicycloundecene.

8. The process of claim 1, wherein ROH in step c) is benzyl alcohol.

9. The process of claim 1, wherein the N-brominating agent in step c) is: 1,3-dibromo-5,5-dimethylhydantoin; n-bromoacetamide; 1-bromo-3-chloro-5,5-dimethylhydantoin; 3-bromo-4,4-dimethyl-2-oxazolidinone; 1-bromo-5,5-dimethylhydantoin; 3-bromo-5,5-dimethylhydantoin; dibromo isocyanuric acid; n-bromoacetamide monohydrate; n-bromocaprolactam; n-bromophthalimide; 3-bromo-1-chloro-5,5-dimethylhydantoin; dibromoisocyanuric acid potassium salt; n-bromoglutarimide; 1,3-dibromo-5-ethyl-5-methylhydantoin; 1-bromo-3,5-dimethyl-5-ethylhydantoin; 1,3-dibromohydantoin; 1,3-dibromo-5-isopropyl-5-methylhydantoin; dibromocyanoacetamide; or 3-bromo-5-methyl-5-phenyl-imidazolidine-2,4-dione.

10. The process of claim 1, wherein ROH in step c) is: MeOH, EtOH, PrOH, i-PrOH, BuOH, i-BuOH or $PhCH_2OH$.

11. The process of claim 1, wherein in step c), the organic base is added at below 30° C., followed by the addition of the N-brominating agent at 45° C. and stirring for 20 minutes at 45° C.

* * * * *